US010438700B2

(12) United States Patent
Ortiz et al.

(10) Patent No.: US 10,438,700 B2
(45) Date of Patent: Oct. 8, 2019

(54) COMPUTER SIMULATION FOR TESTING AND MONITORING OF TREATMENT STRATEGIES FOR STRESS HYPERGLYCEMIA

(71) Applicant: University of Virginia Patent Foundation, Charlottesville, VA (US)

(72) Inventors: Edward A. Ortiz, Charlottesville, VA (US); Stephen D. Patek, Charlottesville, VA (US); Marc D. Breton, Charlottesville, VA (US); Leon S. Farhi, Charlottesville, VA (US); Boris P. Kovatchev, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 927 days.

(21) Appl. No.: 14/419,375

(22) PCT Filed: Aug. 5, 2013

(86) PCT No.: PCT/US2013/053664
§ 371 (c)(1),
(2) Date: Feb. 3, 2015

(87) PCT Pub. No.: WO2014/022864
PCT Pub. Date: Feb. 6, 2014

(65) Prior Publication Data
US 2015/0193589 A1    Jul. 9, 2015

Related U.S. Application Data

(60) Provisional application No. 61/679,430, filed on Aug. 3, 2012.

(51) Int. Cl.
*G01N 33/48*    (2006.01)
*G16H 50/50*    (2018.01)
*C12Q 1/54*    (2006.01)

(52) U.S. Cl.
CPC .............. *G16H 50/50* (2018.01); *C12Q 1/54* (2013.01)

(58) Field of Classification Search
None
See application file for complete search history.

(56) References Cited

U.S. PATENT DOCUMENTS

2005/0125158 A1* 6/2005 Schlessinger ........... G06F 17/18
702/19
2005/0171503 A1 8/2005 Van Den Berghe et al.
(Continued)

FOREIGN PATENT DOCUMENTS

EP    1995680 A2    11/2008

*Primary Examiner* — Larry D Riggs, II
(74) *Attorney, Agent, or Firm* — Vorys, Sater, Seymour and Pease LLP; Vincent M DeLuca; Robert J Decker

(57) ABSTRACT

Time-varying hyperglycemic stresses are derived from actual ICU patients and applied to non-critically ill virtual patients, using any model of normal glucose-insulin physiology that fulfills certain requirements, in order to model and simulate stress hyperglycemia. Other aspects provide: 1) a methodology to perform sensitivity analyses of the parameters of ICU insulin infusion therapy protocols and to improve the protocols; and 2) a training system for clinicians about the course and management of stress hyperglycemia in the ICU or other facility.

19 Claims, 2 Drawing Sheets

(56) References Cited

U.S. PATENT DOCUMENTS

| | | |
|---|---|---|
| 2005/0234311 A1 | 10/2005 | Kouchi et al. |
| 2005/0238581 A1* | 10/2005 | Kurland ................ A61B 1/00 424/9.2 |
| 2006/0147899 A1 | 7/2006 | Famili et al. |
| 2007/0179771 A1 | 8/2007 | Kouchi et al. |
| 2008/0154513 A1* | 6/2008 | Kovatchev ............ G06F 19/345 702/19 |
| 2010/0161299 A1 | 6/2010 | Seike et al. |
| 2010/0198020 A1 | 8/2010 | Alferness et al. |
| 2011/0237917 A1 | 9/2011 | Roy et al. |

* cited by examiner

COMPUTER SIMULATION FOR TESTING AND MONITORING OF TREATMENT STRATEGIES FOR STRESS HYPERGLYCEMIA

This invention was made with government support under award number W81XWH-07-1-0717 by US Army Medical Research Acquisition Activity. The government has certain rights in the invention.

BACKGROUND OF THE INVENTION

Tight glycemic control with insulin therapy protocols in the intensive care unit (ICU) can reduce mortality and morbidity from stress-induced hyperglycemia, but this control comes with the risk of hypoglycemia. Computer simulation can be an essential tool in evaluating protocols for insulin delivery in this setting, and to this end, it is necessary to have mathematical models that explain blood glucose (BG) variability within this patient population.

Many models of normal glucose-insulin physiology have been developed. Examples include models based on the minimal model of Bergman, Cobelli, et al. [1], Hovorka et al.[2], and Dalla Man et al. [3] All have inputs for feeding 101, with parameters that describe an individual or average normal subject 102, and equations 103 that process this information to yield a series of normal BG values 104, as shown in FIG. 1.

There are no models of stress hyperglycemia per se. However, each existing model of normal glucose-insulin physiology can be modified to fit a real ICU patient on a "customized" or patient-by-patient basis in order to create a single, corresponding in silico ICU patient. Such per-patient ICU adaptation of normal glucose-insulin models has been done by Chase et al.[4], using a modified version of Bergman and Cobelli's minimal model, and by Hovorka et al., using a self-developed model [2]. Because their adaptations are not adequately based on the broader principles underlying the physiology of stress hyperglycemia, they must empirically adapt their full model for each real ICU patient to yield only a single "cloned" virtual ICU patient. In addition, this empirical adaptation of each model is specific to each model alone. This severely limits the number, variability, and ease of creation of in silico ICU patients for simulation.

BRIEF SUMMARY OF THE INVENTION

Treatment of stress hyperglycemia has been found to reduce morbidity and mortality in some critically ill patients in intensive care units (ICU). Study of treatment protocols for stress hyperglycemia has been complicated by such things as measurement error, and differences in patient populations and protocol attributes. Computer simulation can safely expedite the study of such variables before further study being considered in real patients. This requires a mathematical model that explains blood glucose (BG) variability in critically ill patients.

A core aspect of an embodiment of the present invention includes, but is not limited to, a method to derive time-varying hyperglycemic stresses from actual ICU patients and to apply them to non-critically ill virtual patients, using any model of normal glucose-insulin physiology that fulfills certain requirements, in order to model and simulate stress hyperglycemia. Other aspects of an embodiment of the present invention, made possible by the exemplary core aspect, provide: 1) a methodology to perform sensitivity analyses of the parameters of ICU insulin infusion therapy protocols and to improve the protocols; and 2) the training system for clinicians about the course and management of stress hyperglycemia in the ICU or other facility.

Referring to Ref. no. 5 (E. A. Ortiz, "Simulation of Glycemic Variability in Critically Ill Burn Patients," National Library of Medicine Trainee Conference, Madison, Wis., Jun. 27, 2012), Applicants investigated the usefulness of computer simulation based on mathematical models and the need to consider the physiology of stress hyperglycemia when modeling and simulating stress hyperglycemia in an ICU.

Accordingly, aspects of an embodiment of the present invention provide a system, method and computer readable medium that, among other things:

Expands the number of underlying models of normal glucose-insulin physiology that can be used for modeling and simulation of critically ill patients Enables comparison of different underlying models of normal glucose-insulin physiology in modeling and simulation of critically ill patients Geometrically increases the number and variability of in silico ICU patients available for simulation Enables abstraction of "stress action profiles" that can themselves be data for further use, such as the development of a model for stress action itself

DETAILED DESCRIPTION OF THE INVENTION

Figure 2:
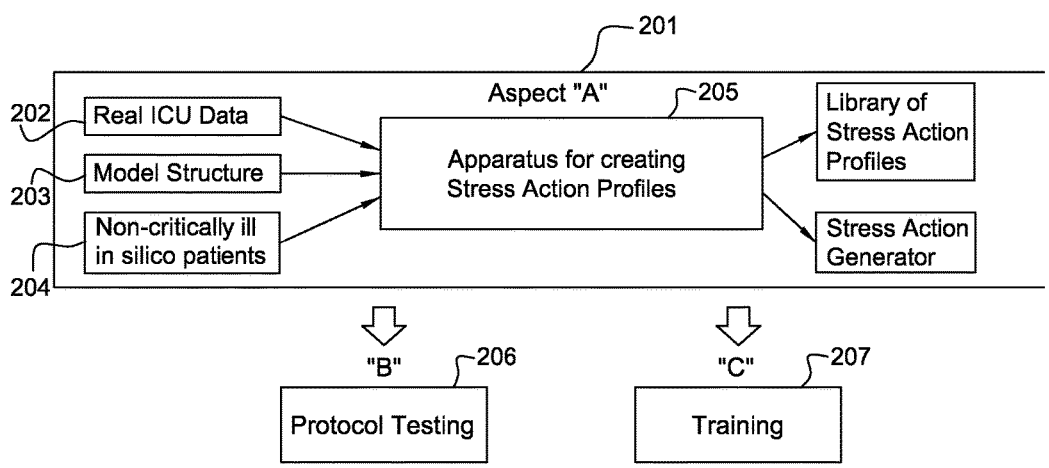
FIG. 2 is a block diagram of a first aspect of the invention.

One embodiment of the present invention has, but is not limited to, several aspects, with a core aspect for instance including an apparatus that makes the other aspects possible. Referring to FIG. 2:

Aspect "A" 201 uses three inputs:

1) clinical data 202 of real ICU patients;

2) a model structure 203 of the glucose-insulin system of non-critically ill subjects; and 3) a broadly varied population 204 of non-critically ill in silico subject parameter sets.

From these inputs the apparatus 205 creates a library of "Stress Action" profiles that accurately reflect stress hyperglycemia in a critical care setting (ICU) in a physiologically justifiable way. Going beyond mere "cloning," each Stress Action profile can then be applied to numerous non-critically ill virtual patients in order to model and simulate stress hyperglycemia in the ICU, generating many in silico ICU patients with high variability. Further, this output of Stress Action profiles can be the foundation for the development of a stochastic generator of unlimited Stress Action profiles, which would enable extended-duration simulation for testing ICU insulin infusion treatment protocols or for studying prediction.

The other aspects of an embodiment of the present invention flow from Aspect "A". Aspect "B" includes apparatus 206 for computing sensitivities of Insulin Infusion Therapy Protocol parameters and for improving such protocols. Aspect "C" is a training system 207 enabled and founded upon "A". The numerous and variable in silico ICU patients generated by the apparatus would be the basis for a teaching instrument for clinicians about the course and management of stress hyperglycemia, including the use of multiple "what-if" scenarios.

Figure 1:
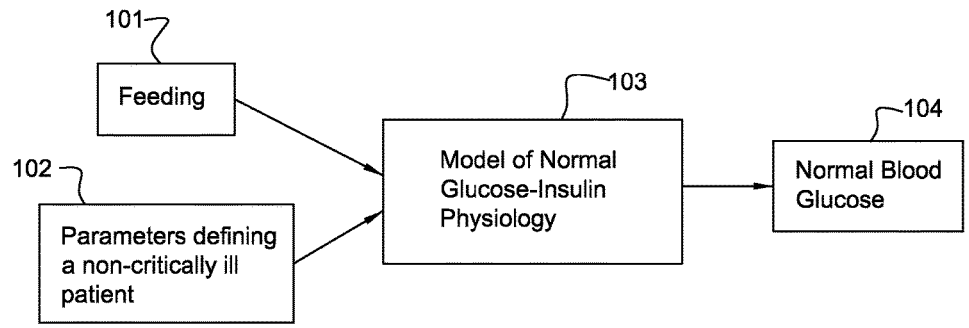
FIG. 1 is a block diagram of a model of normal glucose-insulin physiology, which can be modified in accordance with the present invention to achieve the objectives of the invention.
Figure 3:
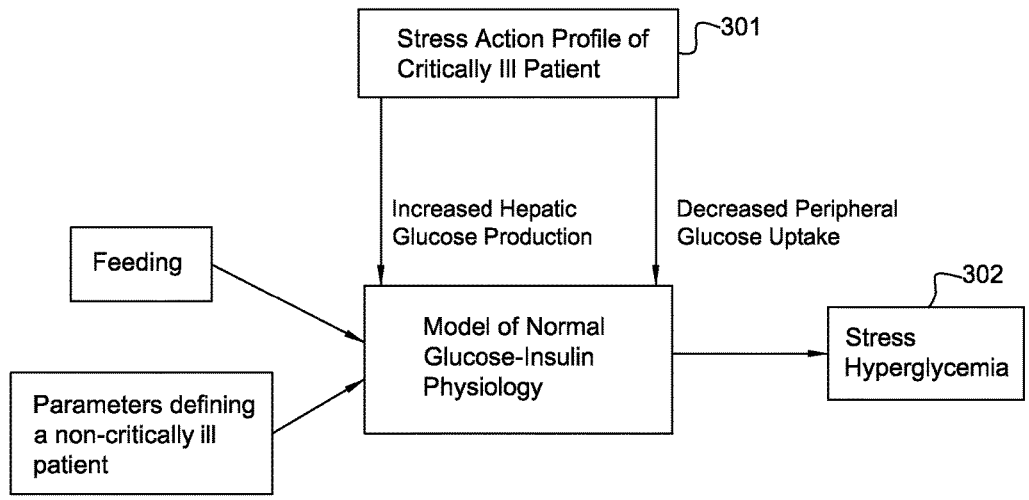
FIG. 3 is a block diagram of an application of Stress Action to non-critically ill subjects to simulate Stress Hyperglycemia, in accordance with the invention.

Detailed Description of Aspect A:

Stress Hyperglycemia is effected by the collective actions of stress hormones on hepatic glucose production (HGP) and peripheral glucose uptake (PGU): HGP is increased and PGU is decreased. There are naturally minimum and maximum rates of HGP and PGU for any given subject, which should be represented in corresponding sites of a glucose-insulin model. If the collective actions of stress hormones on HGP and PGU are assigned to a single time varying coefficient ("SA(t)" or "Stress Action"), it can only assume values between zero (no hyperglycemic effect) and one (maximum hyperglycemic effect) to explain the degree of stress hyperglycemia at each time point. This Stress Action, derived from a real ICU patient, can then be applied extrinsically to numerous, non-critically ill virtual patients. For example, as illustrated in FIG. 3, the Stress Action profile 301 can be applied to the model of normal glucose-insulin physiology as shown in FIG. 1, to obtain a series of stress hyperglycemia BG values 302.

In our work we allowed Stress Action to simultaneously modify both rates (HGP and PGU), because we used the actions of the best-studied hyperglycemic stress hormone, epinephrine, as a stand-in for the collective actions of all the stress hormones. As more is learned about the hyperglycemic effects of the other stress hormones, different time constants may be assigned for each. Also, we weighted the hyperglycemic effect of Stress Action on HGP equal to one, with the weight on PGU at a literature-derived value of 0.65. Sensitivity analysis or new information may change the optimal values for these. Nonetheless, whatever values are ultimately chosen for time constants and weights, the framework for using Stress Action remains valid.

For our method, a mathematical model of normal glucose-insulin physiology is needed that incorporates virtual patient parameter sets reflecting a broadly varied population of non-critically ill subjects. It should explicitly describe insulin-dependent and insulin-independent uptake in hepatic and peripheral tissues. For our application, we used the Glucose-Insulin-Meal model of Dalla Man et al. [3].

Steps in method:

Step 1: Place a new time-varying coefficient (herein referred to as "SA(t)" or "stress action") into the model at the sites of action of the stress hormones, specifically those dealing with hepatic glucose production and insulin-dependent peripheral glucose uptake, such that:

1a) Hepatic Glucose Production is increased by SA(t)× (sum of insulin-dependent and insulin-independent hepatic glucose uptake). SA(t) is constrained to [0 1];

1b) Insulin-dependent Peripheral Glucose Uptake is reduced by a weighting factor×SA(t)×insulin-dependent peripheral glucose uptake. Our application used a literature derived weighting factor of 0.65;

Step 2: Obtain time series data of blood glucose measurements, intravenous insulin administration rates, and feedings from real, critically ill patients;

Step 3: For each combination of non-critically ill virtual patient parameter sets and real patient time series feeding and insulin data:

3a) simulate BG without fitting SA(t) ("plain") and 3b) numerically fit SA(t) such that simulated BG replicates real BG values. Our application used hourly fittings, but other intervals could be used;

Step 4: For each real patient, find the fitted SA(t) vector and virtual patient combination which yields a simulated BG tracing that most closely approximates the real BG tracing. We used Mean Absolute Percentage Error (MAPE), but a different metric could be used. If more than one SA(t) vector and virtual patient combination have the same metric value, then choose the combination whose "plain" simulation most closely approximates the real BG tracing;

Step 5: Create two sets from the above selected combinations of SA(t) and virtual patients:

5a) collection of SA(t) vectors (or "stress action profiles")

5b) collection of unique virtual non-critically ill patient parameter sets;

Step 6: Inputting recombinations of stress action profiles with different non-critically ill virtual patients into a simulator with the chosen model produces simulated stress hyperglycemia of new in silico ICU patients.

Figure 4:
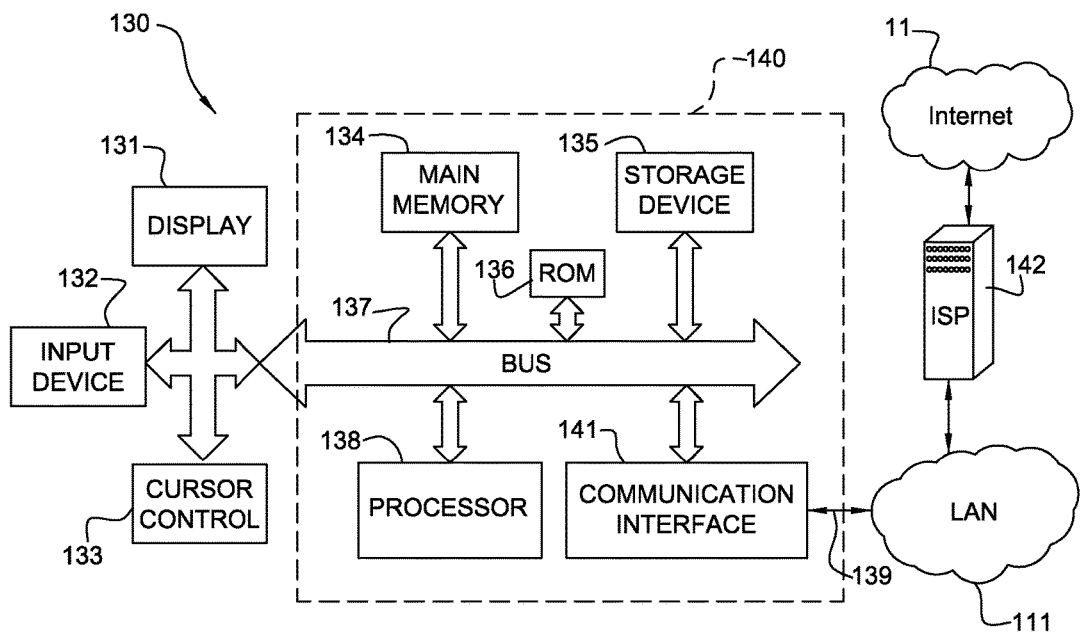
FIG. 4 is a block diagram that illustrates a system for implementing an embodiment of the invention.

FIG. 4 is a block diagram that illustrates a system 130 including a computer system 140 and the associated Internet 11 connection upon which an embodiment of the invention may be implemented. Such configuration is typically used for computers (hosts) connected to the Internet 11 and executing server or client (or a combination server-client) software applications. A source computer such as laptop, an ultimate destination computer and relay servers, for example, as well as any computer or processor described herein, may use the computer system configuration and the Internet connection shown in FIG. 4. The system 140 may be used as a portable electronic device such as a notebook/laptop computer, a media player (e.g., MP3 based or video player), a cellular phone, a Personal Digital Assistant (PDA), an image processing device (e.g., a digital camera or video recorder), and/or any other handheld computing devices, or a combination of any of these devices. Note that while FIG. 4 illustrates various components of a computer system, it is not intended to represent any particular architecture or manner of interconnecting the components; as such details are not germane to the present invention. It FIG. 4 appreciated that network computers, handheld computers, cell phones and other data processing systems which have fewer components or perhaps more components may also be used. The computer system of FIG. 4 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments of the invention are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (02-20-04), which is incorporated in its entirety for all purposes as if fully set forth herein.

Wireless links may also be implemented. In any such implementation, communication interface 141 sends and receives electrical, electromagnetic or optical signals that carry digital data streams representing various types of information.

Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concept of treatment strategies for stress hypoglycemia and the related networks, computer systems, internet, and components and functions may be implemented according to the scheme disclosed herein.

An aspect of various embodiments of the present invention may be utilized for a number of applications, such as but not limited thereto, the following:

Development of a model for stress action itself, which would enable extended-duration simulation for testing treatment protocols or for studying prediction.

Creation of multiple populations of stress action for simulation and testing of treatment protocols As part of a service to study and improve treatment of a specific patient population When applied to different models of normal physiology, can allow comparison of the models for the same patient population to determine the best model for a specific population or application An aspect of various embodiments of the present invention may provide a number of novel and nonobvious features, elements and characteristics, such as but not limited thereto, the following:

Our method (and related system and computer readable medium) converts any mathematical model of normal glucose-insulin physiology that fulfills certain requirements into a model of stress hyperglycemia.

Our method (and related system and computer readable medium) abstracts non-patient-specific hyperglycemic stresses from real ICU patients, making them available for further use.

An aspect of various embodiments of the present invention may provide a number of advantages, such as but not limited thereto, the following:

Expands the number of underlying models of normal glucose-insulin physiology that can be used for modeling and simulation of critically ill patients Enables comparison of different underlying models of normal glucose-insulin physiology in modeling and simulation of critically ill patients Geometrically increases the number and variability of in silico ICU patients available for simulation The abstracted "stress action profiles" can themselves be data for further use, such as the development of a model for stress action itself.

An aspect of various embodiments of the present invention may be utilized for a number of products and services, such as but not limited thereto, the following:

Development of a model for stress action itself, which would enable extended-duration simulation for testing treatment protocols or for studying prediction.

Creation of multiple populations of stress action for simulation and testing of treatment protocols.

As part of a service to study and improve treatment of a specific patient population When applied to different models of normal physiology, can allow comparison of the models for the same patient population to determine the best model for a specific population or application.

PUBLICATIONS

The following patents, applications and publications as listed below and throughout this document are hereby incorporated by reference in their entirety herein.

[1] R. N. Bergman, Y. Z. Ider, C. R. Bowden, and C. Cobelli, "Quantitative estimation of insulin sensitivity," *Am J Physiol Endocrinol Metab*, vol. 236, no. 6, pp. E667-677, 1979.

[2] R. Hovorka, L. J. Chassin, M. Ellmerer, J. Plank, and M. E. Wilinska, "A simulation model of glucose regulation in the critically ill," *Physiological Measurement*, vol. 29, no. 8, pp. 959-978, 2008.

[3] C. D. Man, R. A. Rizza, and C. Cobelli, "Meal simulation model of the glucose-insulin system," *IEEE Transactions on Biomedical Engineering*, vol. 54, no. 10, pp. 1740-1749, 2007.

[4] J. G. Chase, G. M. Shaw, J. Lin, C. V. Doran, C. Hann, M. B. Robertson, P. M. Browne, T. Lotz, G. C. Wake, and B. Broughton, "Adaptive bolus-based targeted glucose regulation of hyperglycaemia in critical care," *Medical Engineering & Physics*, vol. 27, no. 1, pp. 1-11, January 2005

[5] E. A. Ortiz, "Simulation of Glycemic Variability in Critically Ill Burn Patients", National Library of Medicine Trainee Conference, Madison, Wis., Jun. 27, 2012

The devices, systems, computer readable medium, and methods of various embodiments of the invention disclosed herein may utilize aspects disclosed in the following references, applications, publications and patents and which are hereby incorporated by reference herein in their entirety:

A'. International Patent Application Serial No. PCT/US2012/043910, Kovatchev, et al., "Unified Platform For Monitoring and Control of Blood Glucose Levels in Diabetic Patients", filed Jun. 23, 2012.

A". International Patent Application Serial No. PCT/US2012/043883, Kovatchev, et al., "Methods and Apparatus for Modular Power Management and Protection of Critical Services in Ambulatory Medical Devices", filed Jun. 22, 2012.

A. International Patent Application Serial No. PCT/US2011/029793, Kovatchev et al., entitled Method, System, and Computer Program Product for Improving the Accuracy of Glucose Sensors Using Insulin Delivery Observation in Diabetes," filed Mar. 24, 2011

B. PCT/US2011/028163, Breton, et al., entitled "Method and System for the Safety, Analysis and Supervision of Insulin Pump Action and Other Modes of Insulin Delivery in Diabetes", filed Mar. 11, 2011.

C. International Patent Application Serial No. PCT/US2010/047711, Kovatchev, et al., "Tracking the Probability for Imminent Hypoglycemia in Diabetes from Self-Monitoring Blood Glucose (SMBG) Data," filed Sep. 2, 2010.

D. International Patent Application Serial No. PCT/US2010/047386, Kovatchev, et al., "System, Method and Computer Program Product for Adjustment of Insulin Delivery (AID) in Diabetes Using Nominal Open-Loop Profiles", filed Aug. 31, 2010.

E. International Patent Application Serial No. PCT/US2010/040097, Kovatchev, et al., "System, Method, and Computer Simulation Environment for In Silico Trials in Prediabetes and Type 2 Diabetes", filed Jun. 25, 2010.

F. International Patent Application Serial No. PCT/US2010/036629, Kovatchev, et al., "System Coordinator and Modular Architecture for Open-Loop and Closed-Loop Control of Diabetes", filed May 28, 2010 (Publication No. WO 2010/138848, Dec. 2, 2010).

G. International Patent Application Serial No. PCT/US2010/025405, Kovatchev, et al., entitled "Method, System and Computer Program Product for CGM-Based Prevention of Hypoglycemia via Hypoglycemia Risk Assessment and Smooth Reduction Insulin Delivery," filed Feb. 25, 2010.

H. International Patent Application Serial No. PCT/US2009/065725, Kovatchev, et al., filed Nov. 24, 2009, entitled "Method, System, and Computer Program Product for Tracking of Blood Glucose Variability in Diabetes from Data."

I. International Patent Application Serial No. PCT/US2008/082063, Magni, et al., entitled "Model Predictive Control Based Method for Closed-Loop Control of Insulin Delivery in Diabetes Using Continuous Glucose Sensing", filed Oct. 31, 2008; U.S. patent application Ser. No. 12/740,275, Magni, et al., entitled "Predictive Control Based System and Method for Control of Insulin Delivery in Diabetes Using Glucose Sensing", filed Apr. 28, 2010.

J. International Patent Application Serial No. PCT/US2008/069416, Breton, et al., entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008, (Publication No. WO 2009/009528, Jan. 15, 2009); U.S. patent application Ser. No. 12/665,149, Breton, et al., "Method, System and Computer Program Product for Evaluation of Insulin Sensitivity, Insulin/Carbohydrate Ratio, and Insulin Correction Factors in Diabetes from Self-Monitoring Data", filed Dec. 17, 2009.

K. International Patent Application Serial No. PCT/US2008/067725, Kovatchev, et al., entitled "Method, System and Computer Simulation Environment for Testing of Monitoring and Control Strategies in Diabetes," filed Jun. 20, 2008, (Publication No. WO 2008/157781, Dec. 24, 2008); U.S. patent application Publication Ser. No. 12/664,444, Kovatchev, et al., filed Dec. 14, 2009, entitled "Method, System and Computer Simulation Environment for Testing of Monitoring and Control Strategies in Diabetes", (Publication No. 2010/0-179768, Jul. 15, 2010).

L. International Patent Application Serial No. PCT/US2008/067723, Patek, et al., entitled "LQG Artificial Pancreas Control System and Related Method", filed on Jun. 20, 2008.

M. U.S. patent application Ser. No. 12/516,044, Kovatchev, et al., filed May 22, 2009, entitled "Method, System, and Computer Program Product for the Detection of Physical Activity by Changes in Heart Rate, Assessment of Fast Changing Metabolic States, and Applications of Closed and Open Control Loop in Diabetes".

N. International Patent Application Serial No. PCT/US2007/085588, Kovatchev, et al., filed Nov. 27, 2007, entitled "Method, System, and Computer Program Product for the Detection of Physical Activity by Changes in Heart Rate, Assessment of Fast Changing Metabolic States, and Applications of Closed and Open Control Loop in Diabetes", (Publication No. WO2008/067284, Jun. 5, 2008)

O. U.S. patent application Ser. No. 11/943,226, Kovatchev, et al., filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes".

P. U.S. patent application Ser. No. 11/578,831, Kovatchev, et al., filed Oct. 18, 2006 entitled "Method, System and Computer Program Product for Evaluating the Accuracy of Blood Glucose Monitoring Sensors/Devices", (Publication No. US2007/0232878, Oct. 4, 2007), U.S. Pat. No. 7,815,569, Kovatchev, et al., issued Oct. 29, 2010

Q. International Application Serial No. PCT/US2005/013792, Kovatchev, et al., filed Apr. 21, 2005, entitled "Method, System, and Computer Program Product for Evaluation of the Accuracy of Blood Glucose Monitoring Sensors/Devices", (Publication No. WO 05106017, Nov. 10, 2005

R. International Patent Application Serial No. PCT/US01/09884, Kovatchev, et al., filed Mar. 29 2001, entitled "Method, System, and Computer Program Product for Evaluation of Glycemic Control in Diabetes Self-Monitoring Data", (Publication No. WO 01/72208, Oct. 4, 2001).

S. U.S. patent application Ser. No. 10/240,228, Kovatchev, et al., filed Sep. 26, 2002, (Publication No. 0212317, Nov. 13, 2003), U.S. Pat. No. 7,025,425 B2, Kovatchev, et al., issued Apr. 11, 2006, entitled "Method, System, and Computer Program Product for the Evaluation of Glycemic Control in Diabetes from Self-Monitoring Data".

T. U.S. patent application Ser. No. 11/305,946, Kovatchev, et al., filed Dec. 19, 2005 entitled "Method, System, and Computer Program Product for the Evaluation of Glycemic Control in Diabetes from Self-Monitoring Data" (Publication No. 2006/0094947, May 4, 2006), U.S. Pat. No. 7,874,985, Kovatchev, et al., issued Jan. 25, 2011.

U. U.S. patent application Ser. No. 12/975,580, Kovatchev, et al., "Method, System, and Computer Program Product for the Evaluation of Glycemic Control in Diabetes from Self-Monitoring Data", filed Dec. 22, 2010.

V. International Patent Application Serial No. PCT/US2003/025053, Kovatchev, et al., filed Aug. 8, 2003, entitled "Method, System, and Computer Program Product for the Processing of Self-Monitoring Blood Glucose (SMBG) Data to Enhance Diabetic Self-Management", (Publication No. WO 2004/015539, Feb. 19, 2004).

W. U.S. patent application Ser. No. 10/524,094, Kovatchev, et al., filed Feb. 9, 2005 entitled "Managing and Processing Self-Monitoring Blood Glucose" (Publication No. 2005/214892, Sep. 29, 2005).

X. U.S. patent application Ser. No. 12/065,257, Kovatchev, et al., filed Aug. 29, 2008, entitled "Accuracy of Continuous Glucose Sensors", (Publication No. 2008/0314395, Dec. 25, 2008).

Y. International Patent Application Serial No PCT/US2006/033724, Kovatchev, et al., filed Aug. 29, 2006, entitled "Method for Improvising Accuracy of Continuous Glucose Sensors and a Continuous Glucose Sensor Using the Same", (Publication No. WO 07027691, Mar. 8, 2007).

Z. U.S. patent application Ser. No. 12/159,891, Kovatchev, B., filed Jul. 2, 2008, entitled "Method, System and Computer Program Product for Evaluation of Blood Glucose Variability in Diabetes from Self-Monitoring Data", (Publication No. 2009/0171589, Jul. 2, 2009).

AA. International Application No. PCT/US2007/000370, Kovatchev, B., filed Jan. 5, 2007, entitled "Method, System and Computer Program Product for Evaluation of Blood Glucose Variability in Diabetes from Self-Monitoring Data", (Publication No. WO 07081853, Jul. 19, 2007).

BB. U.S. patent application Ser. No. 11/925,689 and PCT International Patent Application No. PCT/US2007/082744, Breton, et al., both filed Oct. 26, 2007, entitled "For Method, System and Computer Program Product for Real-Time Detection of Sensitivity Decline in Analyte Sensors", (Publication Nos. 2008/0172205, Jul. 17, 2008 and WO 2008/052199, May 2, 2008).

CC. U.S. patent application Ser. No. 10/069,674, Kovatchev, et al., filed Feb. 22, 2002, entitled "Method and Apparatus for Predicting the Risk of Hypoglycemia".

DD. International Application No. PCT/US00/22886, Kovatchev, et al., filed Aug. 21, 2000, entitled "Method and Apparatus for Predicting the Risk of Hypoglycemia", (Publication No. WO 01/13786, Mar. 1, 2001).

EE. U.S. Pat. No. 6,923,763 B1, Kovatchev, et al., issued Aug. 2, 2005, entitled "Method and Apparatus for Predicting the Risk of Hypoglycemia".

FF. U.S. Patent Application Publication No. US 2004/0254434 A1, "Glucose Measuring Module and "Insulin Pump Combination", published Dec. 16, 2004., Goodnow, et al. Ser. No. 10/458,914, filed Jun. 10, 2003.

GG. U.S. Patent Application Publication No. US 2009/00697456 A1, Estes, et al., "Operating an Infusion Pump System", published Mar. 12, 2009. Ser. No. 11/851,194, Sep. 6, 2007.

HH. Fernandez-Luque, et al., eDiab: A System for Monitoring, Assisting and Educating People with Diabetes", ICCHP 2006, LNCS 4061, pp. 1342-1349, 2006.

II. U.S. Pat. No. 6,602,191 B2, Quy, R., Method and Apparatus for Health and Disease Management Combining Patient Data Monitoring with Wireless Internet Connectivity, Aug. 5, 2003.

JJ. International Patent Application Publication No. WO 2008/064053 A2, Patel, et al., Systems and Methods for Diabetes Management Using Consumer Electronic Devices, May 29, 2008; International Patent Application Serial No. PCT/US2007/084769, filed Nov. 15, 2007.

KK. International Patent Application Publication No. WO 2010/138817 A1, Ow-Wing, K., Glucose Monitoring System with Wireless Communications, Dec. 2, 2010; International Patent Application Serial No. WO 2010/138817 A1, filed May 28, 2010.

LL. International Patent Application Publication No. WO 2004/052204 A1, Kim, Kwan-Ho, Blood Glucose Monitoring System, Jun. 24, 2004; International Patent Application Serial No. PCT/KR2003/000398, filed Feb. 28, 2003.

What is claimed is:

1. A computer-implemented method for testing of monitoring and/or treatment strategies for patients experiencing stress hyperglycemia, comprising:
    providing a computer-executable mathematical model of the human glucose-insulin metabolic system and a database of a population of simulated human subjects collectively having a set of metabolic parameters with values encompassing a distribution of observed parameters in subjects not experiencing stress hyperglycemia;
    adding a time-varying coefficient representing collective action of stress hormones on hepatic glucose production (HGP) and peripheral glucose uptake (PGU), into said model at points modeling action of HGP and PGU, to obtain a modified model;
    obtaining a time-series of simulated blood glucose (BG) values for said population of simulated subjects using said model;
    fitting said time-varying coefficient to said simulated BG values such that said simulated BG values replicate real BG values obtained from actual stress hyperglycemia patients to obtain a set of time-varying coefficient vectors;
    correlating time-varying coefficient vectors and virtual subject data with real patient data to obtain stress action profiles;
    determining effects of said stress hormones on stress hyperglycemia by applying various combinations of stress action profiles and virtual population data in said modified model in a computer processor;
    identifying a treatment protocol for a patient experiencing stress hyperglycemia by comparing a stress action profile of said patient with said obtained stress action profiles; and
    treating said patient for effects of stress hyperglycemia with a treatment protocol associated with an obtained stress action profile corresponding to the stress action profile of said patient.

2. The method of claim 1, wherein said time-varying coefficient is chosen such that HGP is increased.

3. The method of claim 2, wherein HGP is a sum of insulin-dependent and insulin-independent hepatic glucose uptake.

4. The method of claim 2, wherein HGP is constrained to the interval [0 1].

5. The method of claim 1, wherein said time-varying coefficient is chosen such that PGU is reduced.

6. The method of claim 5, wherein PGU is reduced by a weighting factor.

7. The method of claim 6, wherein said weighting factor is 0.65.

8. The method of claim 6, wherein PGU is insulin-dependent peripheral glucose uptake.

9. The method of claim 1, wherein said time-varying coefficients are correlated with real patient data using a Mean Absolute Percentage Error (MAPE) metric.

10. A computer simulation system for testing of monitoring and/or treatment strategies for patients experiencing stress hyperglycemia, comprising:
  a computer module including a mathematical model of the human glucose-insulin metabolic system;
  a database a population of simulated human subjects collectively having a set of metabolic parameters with values encompassing a distribution of observed parameters in subjects not experiencing stress hyperglycemia, and;
  a computer processor programmed to:
    add a time-varying coefficient representing collective action of stress hormones on hepatic glucose production (HGP) and peripheral glucose uptake (PGU), into said model at points modeling action of HGP and PGU, to obtain a modified model;
    obtain a time-series of simulated blood glucose (BG) values for said population of simulated subjects using said model;
    fit said time-varying coefficient to said simulated BG values such that said simulated BG values replicate real BG values obtained from actual stress hyperglycemia patients to obtain a set of time-varying coefficient vectors; and
    correlate time-varying coefficient vectors and virtual subject data with real patient data to obtain stress action profiles; and determine effects of said stress hormones on stress hyperglycemia by applying various combinations of stress action profiles and virtual population data in said modified model;
  wherein a treatment protocol for a patient experiencing stress hyperglycemia is identified by comparing a stress action profile of said patient with said obtained stress action profiles; and
  said patient is treated for effects of stress hyperglycemia with said identified treatment protocol associated with an obtained stress action profile corresponding to the stress action profile of said patient.

11. The system of claim 10, wherein said time-varying coefficient is chosen such that HGP is increased.

12. The system of claim 11, wherein HGP is a sum of insulin-dependent and insulin independent hepatic glucose uptake.

13. The system of claim 11, wherein HGP is constrained to the interval [0 1].

14. The system of claim 10, wherein said time-varying coefficient is chosen such that PGU is reduced.

15. The system of claim 14, wherein PGU is reduced by a weighting factor.

16. The system of claim 15, wherein said weighting factor is 0.65.

17. The system of claim 15, wherein PGU is insulin-dependent peripheral glucose uptake.

18. The system of claim 10, wherein said time-varying coefficients are correlated with real patient data using a Mean Absolute Percentage Error (MAPE) metric.

19. A computer program product comprising a non-transitory computer readable medium having computer readable data and executable instructions stored therein for enabling at least one processor in a computer system for monitoring and/or treatment strategies for patients experiencing stress hyperglycemia using a computer simulation environment, said data comprising a database of a population of simulated human subjects collectively having a set of metabolic parameters with values encompassing a distribution of observed parameters in subjects not experiencing stress hyperglycemia;
  instructions representing a mathematical model of the human glucose-insulin metabolic system; and
  instructions for:
    causing a processor to add a time-varying coefficient representing collective action of stress hormones on hepatic glucose production (HGP) and peripheral glucose uptake (PGU), into said model at points modeling action of HGP and PGU, to obtain a modified model;
    causing a processor to obtain a time-series of simulated blood glucose (BG) values for said population of simulated subjects using said model;
    causing a processor to fit said time-varying coefficient to said simulated BG values such that said simulated BG values replicate real BG values obtained from actual stress hyperglycemia patients to obtain a set of time-varying coefficient vectors;
    causing a processor to correlate time-varying coefficient vectors and virtual subject data with real patient data to obtain stress action profiles; and
    causing a processor to determine effects of said stress hormones on stress hyperglycemia by applying various combinations of stress action profiles and virtual population data in said modified model;
  wherein a treatment protocol for a patient experiencing stress hyperglycemia is identified by comparing a stress action profile of said patient with said obtained stress action profiles; and
  said patient is treated for effects of stress hyperglycemia with said identified treatment protocol associated with an obtained stress action profile corresponding to the stress action profile of said patient.

* * * * *